United States Patent [19]

Roshdy et al.

[11] Patent Number: 5,199,561

[45] Date of Patent: Apr. 6, 1993

[54] PACKAGE FOR ENDOSCOPIC NEEDLE AND SUTURE AND CANNULA ASSEMBLY

[75] Inventors: Constance E. Roshdy, New Egypt, N.J.; Robert J. Cerwin, Pipersville, Pa.

[73] Assignee: Ethicon, Inc., Somerville, N.J.

[21] Appl. No.: 836,497

[22] Filed: Feb. 18, 1992

[51] Int. Cl.⁵ .............................................. A61L 17/02
[52] U.S. Cl. .................................. 206/63.3; 206/227; 206/382
[58] Field of Search ....................... 206/63.3, 227, 380, 206/382

[56] References Cited

U.S. PATENT DOCUMENTS

| | | |
|---|---|---|
| 4,249,656 | 2/1981 | Cerwin et al. . |
| 4,412,614 | 11/1983 | Ivanov et al. . |
| 4,483,487 | 11/1984 | Cerwin et al. . |
| 4,491,218 | 1/1985 | Aday . |
| 4,496,045 | 1/1985 | Ferguson et al. . |
| 4,533,041 | 8/1985 | Aday et al. . |
| 4,549,649 | 10/1985 | Roshdy . |
| 4,555,016 | 11/1985 | Aday et al. . |
| 4,572,363 | 2/1986 | Alpern . |
| 4,615,435 | 10/1986 | Alpern et al. . |
| 4,884,681 | 12/1989 | Roshdy et al. . |
| 4,887,710 | 12/1989 | Roshdy et al. . |
| 4,896,767 | 1/1990 | Pinheiro .................... 206/63.3 |
| 4,946,043 | 8/1990 | Roshdy et al. . |
| 5,024,322 | 6/1991 | Holzwarth .................. 206/63.3 |
| 5,048,678 | 9/1991 | Chambers . |
| 5,082,112 | 1/1992 | Dunklee . |

Primary Examiner—Bryon P. Gehman
Attorney, Agent, or Firm—Emil Richard Skula

[57] ABSTRACT

A foldable package for an endoscopic needle and suture and cannula assembly comprising a central panel and a plurality of foldably attached panels for receiving and retaining the cannula and suture. A needle park is provided for receiving and retaining the needle. Locking means in outer panels fasten the package closed. A tab on the central panel retains the suture in an open loop configuration, while locking tabs and a slot in at least one inner panel retain the cannula.

15 Claims, 5 Drawing Sheets

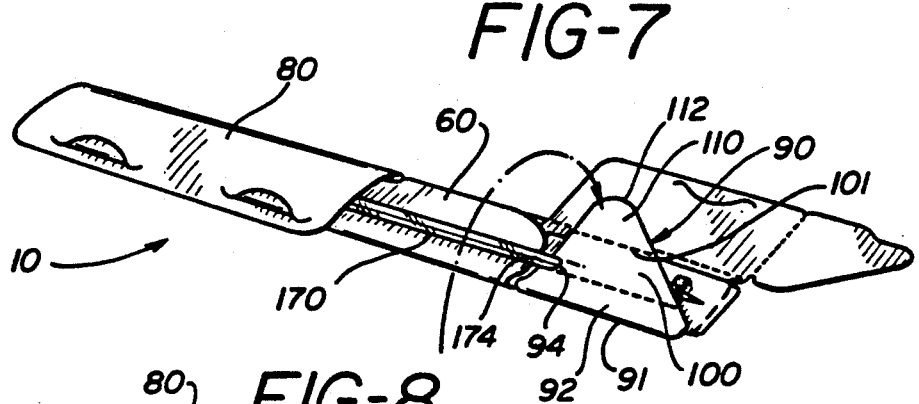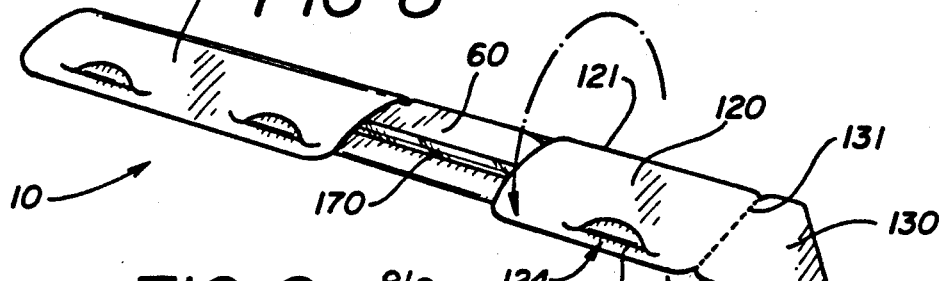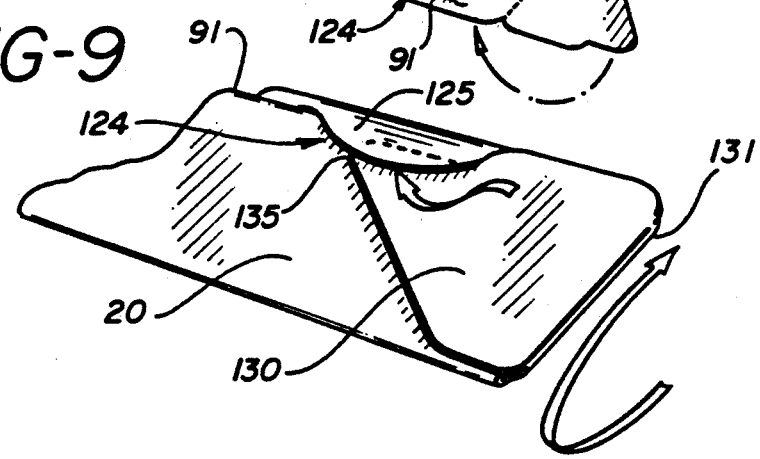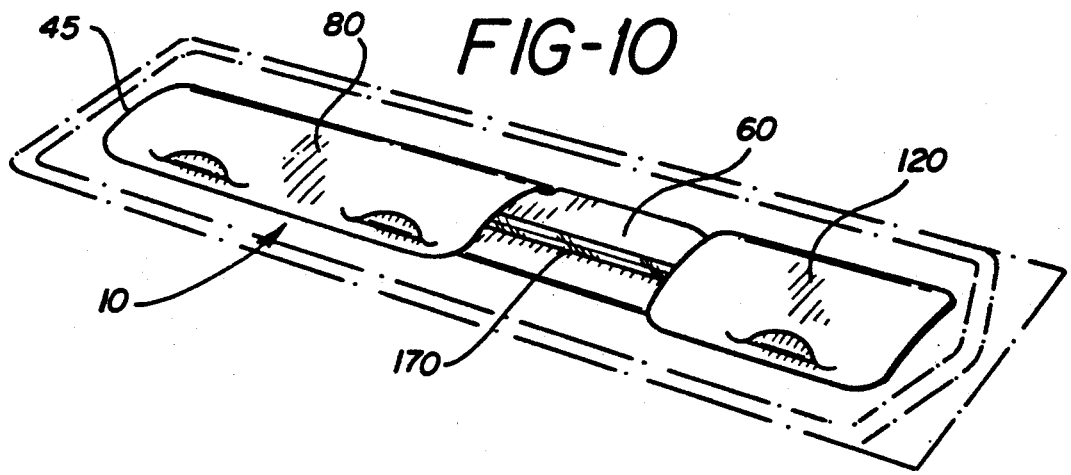

PACKAGE FOR ENDOSCOPIC NEEDLE AND SUTURE AND CANNULA ASSEMBLY

The field of art to which this invention pertains is packaging, in particular packages for endoscopic surgical needle and suture and cannula assemblies.

BACKGROUND OF THE INVENTION

The field of endoscopic surgery is a dynamic area in which major advances in both surgical procedures and instrumentation are occurring. Endoscopic surgical procedures are gaining wide acceptance among the medical profession, health care insurers, and patients because of the many advantages associated with the employment of these procedures. One major advantage is that any incisions which have to be made into the fascia and musculature of a patient in order to perform an endoscopic surgical procedure are of de minimis size in comparison with the radical incisions required in conventional, open surgical techniques. Endoscopic surgical procedures not only reduce the trauma to the patient, but result in reduced avenues for infection and improved rates of recovery. It is not unusual for patients undergoing endoscopic procedures to be either treated on an out-patient basis, or to leave the hospital after a one or two day stay. In contrast, procedures involving conventional, open surgical techniques wherein major, radical, incisions are made in order to access a body cavity or joint, such as a knee, require lengthy recuperative post-operative stays because of the trauma resulting from the radical surgical procedures. In addition, it can be appreciated that during conventional surgical procedures, the avenues for infection are greatly increased, and the interior sections of the body where the procedure is being performed are stressed by being unnaturally exposed to a foreign environment of both ambient air and ambient contaminants.

It is common to perform endoscopic surgical procedures by initially inserting a trocar assembly through the fascia and musculature of the patient in order to access the internal operative site such as the abdominal cavity. The trocar assembly typically comprises an elongated obturator having a sharp tip for piercing. The obturator is concentrically housed within a cylindrical cannula tube. After insertion, the obturator is removed from the cannula tube thereby providing a pathway to the interior of the patient through the cannula tube. Numerous endoscopic surgical instruments can be inserted through the trocar cannula including endoscopic fiber optic light pathways, surgical staplers, cutting and ligating instruments and the like. As with all surgery, it is often necessary to suture incisions made during the endoscopic operative procedure. In order to facilitate suturing, surgical needle and suture and cannula assemblies have been developed. The assemblies typically consist of a surgical needle having one end of a suture affixed thereto. The other end of the suture is run through a cannula and is affixed to the proximal end of the cannula. During surgery, the surgeon grasps the needle and suture using endoscopic surgical grasping instruments and inserts the needle and suture through a trocar cannula to the operative site. There, the needle and suture can be inserted into and out of tissue; e.g., at either side of an incision. Then the needle is grasped by the grasping instrument and withdrawn along with a length of suture from the patient through the trocar cannula. Exterior to the patient, the surgeon places a knot in the suture by manipulating both ends of the suture. Once the knot has been tied and the needle has been cut from the suture, the proximal end of the cannula is broken, allowing the cannula to be displaced or slide with respect to the suture. The cannula is then used as a knot pusher to push the knot through the trocar cannula along the suture into the interior of the patient and to the operative site to securely knot the suture, thus completing the desired suturing function such as joining tissue, ligating vessels and the like. The suture is then cut and the excess suture and cannula are removed from the patient.

It is extremely important that the needle and suture and cannula assembly be packaged in a manner such that the suture material is retained in a fairly straight configuration. It is also important that the cannula and suture and needle assembly be held and retained in a manner such that it will not be damaged during sterilization procedures, packaging, handling and storage. It is also important that the cannula and suture and needle assembly be readily and easily removable from the package in an essentially continuous motion without damage to the device.

Packages for needle and suture and cannula assemblies are known in the art, however, these packages have several disadvantages. First of all, the packages tend to allow the suture material to move about the package during shipping, handling, and sterilization procedures, thereby allowing the suture material to become kinked or otherwise misshaped and, therefore undesirable for use in endoscopic surgical procedures. In addition, it is very difficult for operating room personnel to remove the cannula and needle and suture assembly in an easy manner from the prior art packages. Finally, these packages do not prevent the inadvertent tearing or puncturing of a plastic overwrap by the cannula which can occur as a result of mishandling of the packaged device.

What is needed in this art is a foldable package for a surgical needle and suture and cannula assembly used in endoscopic surgical procedures which protects and retains the needle and suture and cannula, but yet allows for easy removal of the suture and needle and cannula from the package.

SUMMARY OF THE INVENTION

It is an object of the present invention to provide a foldable package for an endoscopic needle and suture and cannula assembly which protects the needle and suture and cannula assembly during sterilization, shipping and handling, but which allows the assembly to be readily removed from the package.

It is another object of this invention to provide a package for an endoscopic surgical needle and suture and cannula assembly which is economic to manufacture.

It is a further object of the present invention to provide a package for such an assembly which prevents the assembly from damaging an outerwrap package.

A package for an endoscopic surgical needle and suture and cannula assembly is disclosed. The package comprises a central panel for receiving and holding the assembly. The central panel has a plurality of flaps attached thereto. The central panel has a pair of opposed major sides and a pair of opposed minor sides. A first suture retaining panel is foldably attached to a first major side of the panel along the central section of the first side. An outer cannula retaining panel is foldably connected to the first major side of the central panel below the first suture retaining panel. An upper, outer locking panel is foldably connected to the central panel above the first suture retaining panel. An inner suture retaining panel is foldably connected to the second major side of the central panel. A triangularly shaped cannula retaining panel is foldably connected to the second major side of the central panel above the inner suture retaining panel. An end tab panel is foldably connected to the lower minor side of the central panel, optionally forming a gusset between the end tab panel and the central panel. The central panel has a tab extending from its upper minor side for retaining the suture. There are locking means in the triangularly shaped panel for retaining the cannula and locking means in the outer cannula retaining panel and the upper, outer locking panel for fastening the package. In addition, a needle park means on the central panel receives and retains the surgical needle.

Other features and advantages of the invention will become more apparent from the following description and accompanying drawings.

BRIEF DESCRIPTION OF THE DRAWINGS

FIGS. 4-9 are perspective views of the package of the present invention illustrating the step-by-step assembly of the package about the needle and suture and cannula assembly.

FIG. 10 is a perspective view of the package of the present invention containing a surgical needle and suture and cannula assembly in a completely assembled configuration.

BEST MODE FOR CARRYING OUT THE INVENTION

Figure 1:
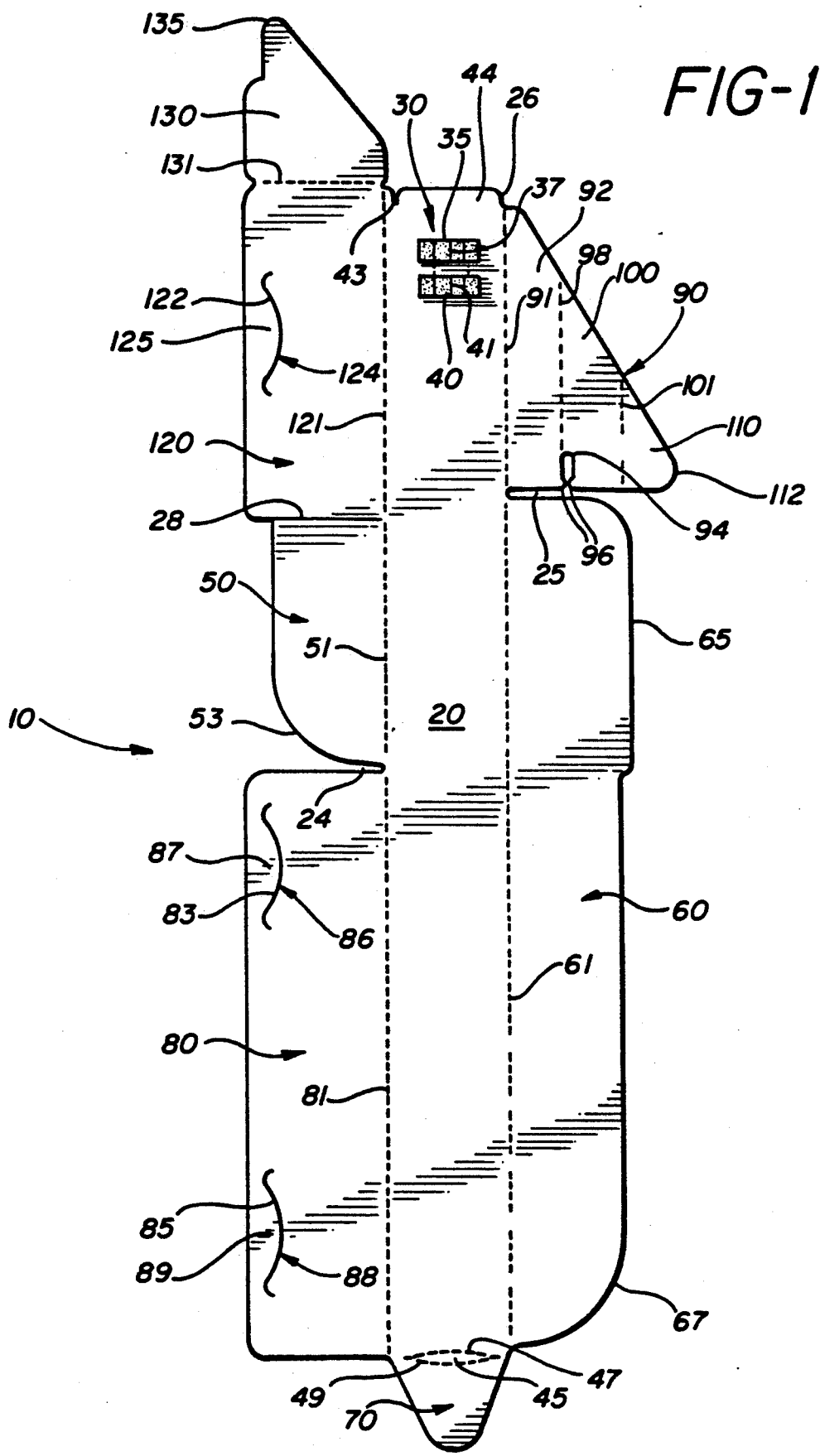
FIG. 1 is a plan view of a package of the present invention prior to folding.
Figure 2:
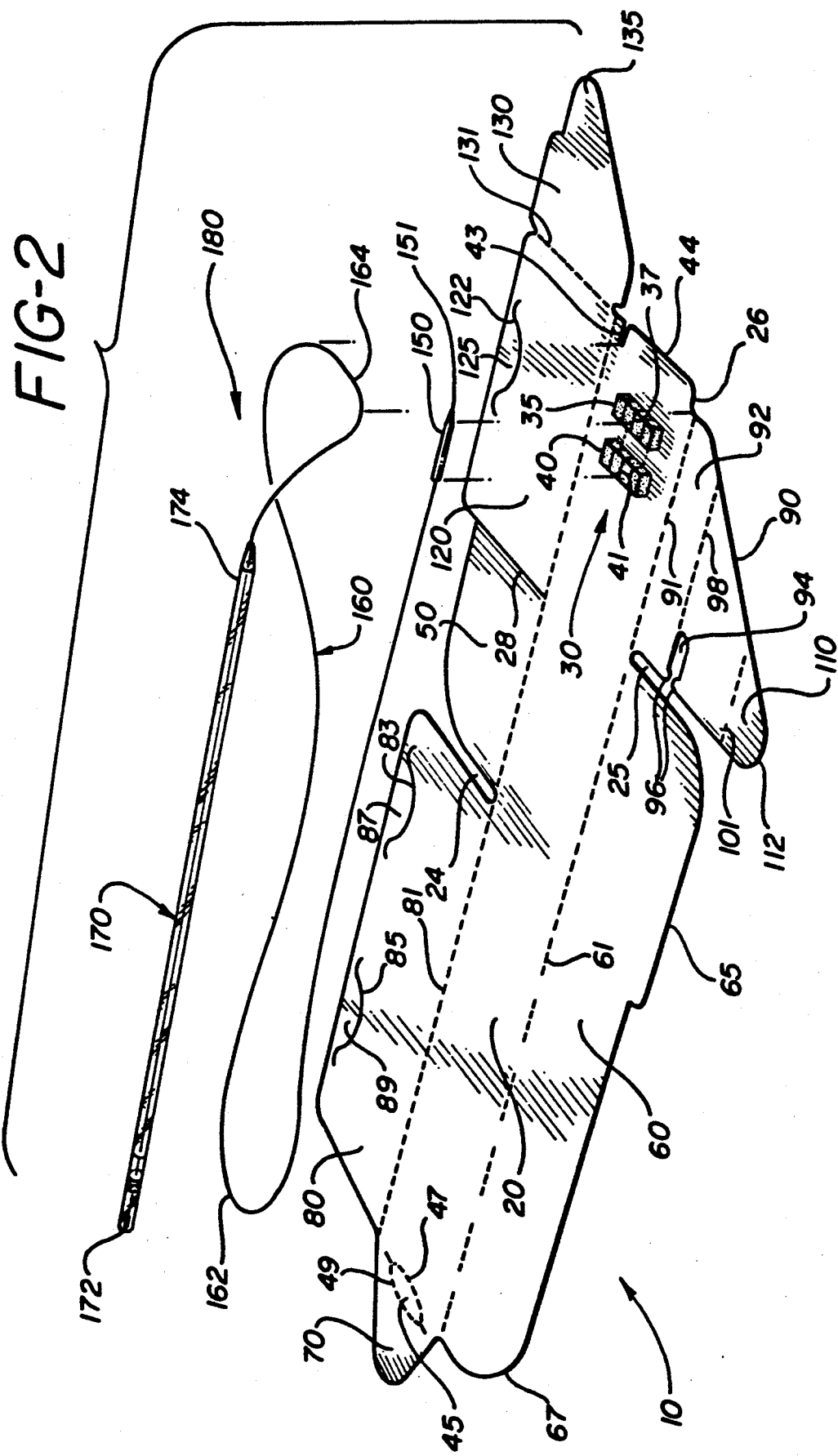
FIG. 2 is a perspective view of a package of the present invention and a surgical needle and suture and cannula assembly prior to folding and assembling the package.

FIG. 1 and FIG. 2 illustrate a package 10, prior to folding, which is a preferred embodiment of the present invention. The package has a top inner side and a bottom outer side. Package 10 has central panel 20 for holding and receiving a surgical needle, suture and cannula assembly 180. Central panel 20 is preferably substantially rectangular in shape and has a pair of opposed major sides and a pair of opposed minor sides. At the upper, top minor side of the central panel 20 is the tab 44 which is formed on one side by U-shaped slot 43 and on the other side by the upper part 26 of the second major side of the central panel 20. The second major side of central panel 20 has been cut inwardly so that the tab 44 is centered on central panel 20. Also centrally located at the top of the central panel 20 is the needle park 30 formed by foam members 40 and 35. Foam member 35 has slits 37 perpendicular to its major longitudinal axis, and, foam member 40 similarly has slits 41. Together the slits and foam members form a needle park 30 for receiving and retaining a surgical needle. Optional score lines 22 mark the location of needle park 30. Foldably connected to the bottom minor side of the central panel 20 is the end tab panel 70. The end panel 70 is foldably connected to the central panel 20 by fold lines 47 and 49. Fold lines 47 and 49 define the end gusset 45, and are co-aligned at either end of the end gusset 45.

Foldably connected to the first major side of central panel 20 are the outer cannula retaining panel 80, the first suture retaining panel 50, and the upper, outer locking panel 120. Foldably connected along the opposite, second major side of central panel 20 are the triangularly shaped cannula retaining panel 90 and the inner suture retaining panel 60.

First suture retaining panel 50 is foldably connected to the central panel 20 along fold line 51. The first suture retaining panel 50 has a curved lower end 53. The first suture retaining panel 50 is separated from outer cannula retaining panel 80 by slot 24. The first suture retaining panel 50 is separated from upper, outer locking panel 120 by slit 28. The inner suture retaining panel 60 is foldably attached to the second major side of central panel 20 along fold line 61. Inner suture retaining panel 60 is disposed substantially opposite to first suture retaining panel 50 and outer cannula retaining panel 80. The panel 60 has an extended tab portion 65 and lower curved end 67. Inner suture retaining panel 60 is separated from the triangularly shaped cannula retaining panel 90 by slot 25. The triangularly shaped cannula retaining panel 90 is foldably connected to the central panel 20 along fold line 91. It will be noted that the top of the panel 90 is attached to the side of the central panel 20 immediately below the top minor side of the central panel 20 in order to form, along with slot 43 and the upper part 26, the tab 44.

The triangularly shaped cannula retaining panel 90 is divided into first panel 92, second panel 100, and tab panel 110. The first panel 92 is foldably connected to the second panel 100 along fold line 98. The outer tab panel 110 is foldably connected to second panel 100 along fold line 101. The U-shaped slot 94 is centrally located in the bottom side of cannula retaining panel 90. Tabs 96 are located on opposite sides of the bottom of the opening of u-shaped slot 94. A first tab 96 extends into slot 94 from the first panel 92 while a second opposed tab extends into slot 94 from the second panel 100. Tab panel 110 has end 112.

The outer cannula retaining panel 80 is foldably connected to the first major side of the central panel 20 along fold line 81. The outer cannula retaining panel 80 is located at the bottom of the first major side of central panel 20 directly below the central retaining panel 50. Slot 24 separates central retaining panel 50 from the outer cannula retaining panel 80. The outer cannula retaining panel 80 has a pair of slits 83 and 85 disposed toward its outer edge. The slits 83 and 85 form the tabs 87 and 89 respectively. The slit 83 and the tab 87 form tab pocket 86, while the slit 85 and the tab 89 form tab pocket 88.

The upper, outer locking panel 120 is foldably connected to central panel 20 along the fold line 121. The upper, outer locking panel 120 is separated from tab 44 by slot 43. Upper, outer locking panel 120 is disposed substantially opposite to the triangularly shaped cannula retaining panel 90. The upper, outer locking panel 120 is also situated immediately above first suture retaining panel 50, and is separated from first suture retaining panel 50 by slit 28. Upper, outer locking panel 120 has slit 122 disposed centrally toward its outer edge. Slit 122 forms tab 125. Slit 122 and tab 125 together form tab pocket 124. Optional tab panel 130 is foldably connected to the top of upper, outer locking panel 120 at fold line 131. Tab panel 130 has outer end tab 135 and shoulder 137.

With regard to needle park 30, the foam members 35 and 40 may be affixed to the upper end of the central panel 20 proximate to score lines 22 by conventional methods typical in this art. For example, the foam needle panels may be glued, or mechanically attached. It is particularly preferred in the practice of the present invention to utilize rectangular foam strips having an adhesive pre-applied onto one side. The foam strips are then cut into foam members 35 and 40 having the desired sizes using conventional cutting equipment and processes. Similarly, the slits 37 and 41 are cut into the sides of the foam members not having an adhesive. Then, the adhesive side is affixed to the desired location on the central panel. The foam members 35 and 40 will be of sufficient size and shape to effectively retain and protect the surgical needle. In a preferred embodiment of the present invention, two separate foam members are used, however it will be appreciated by those skilled in the art that the two foam members 35 and 40 can be replaced with a single continuous piece of foam. If one were willing to accept any disadvantages which may be attendant, foam members 35 and 40 may be replaced by paper members.

It will also be appreciated by those skilled in the art that various shapes can be effectively used for the needle park 30, including squares, circles, etc. It will also be appreciated by those skilled in the art that the locking means used to secure the package 10 may include any conventional means in addition to tabs and tab pockets, such as mechanical fasteners, etc., if one were willing to accept any attendant disadvantages.

Referring to FIG. 1 and FIG. 2, the endoscopic needle and suture and cannula assembly 180 is seen to have a cannula 170 with a proximal end 172 and a distal end 174. A suture 160 runs through the cannula 170 and is affixed at one end 166 to the distal end 172 of cannula 170 and at the other end 168 to surgical needle 150. Surgical needle 150 has tip 151 and receiving end 152 for receiving the end 168 of suture 160.

Figure 4:
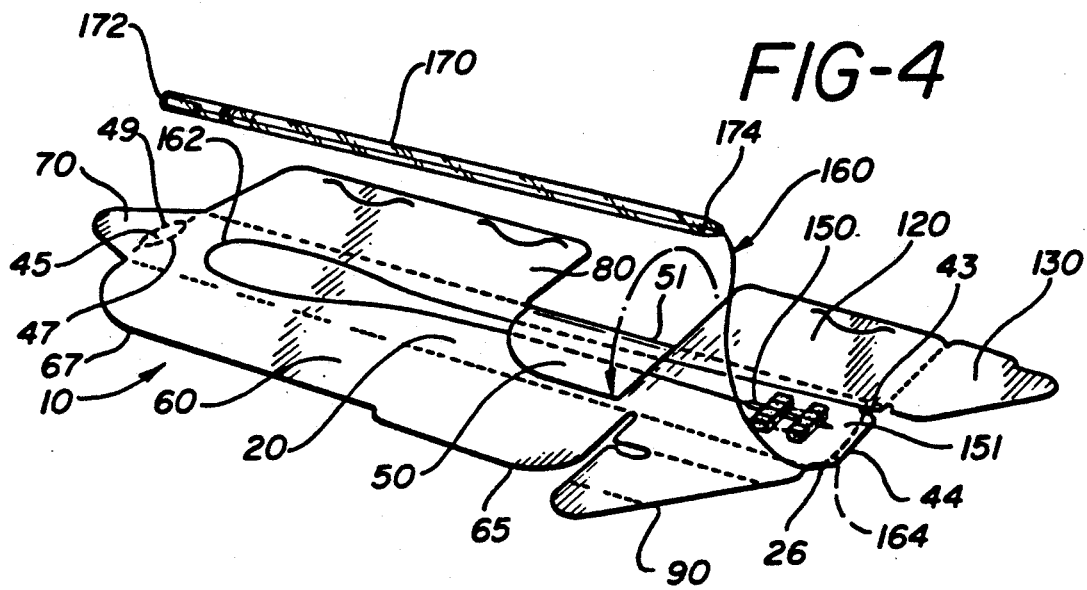
Figure 5:
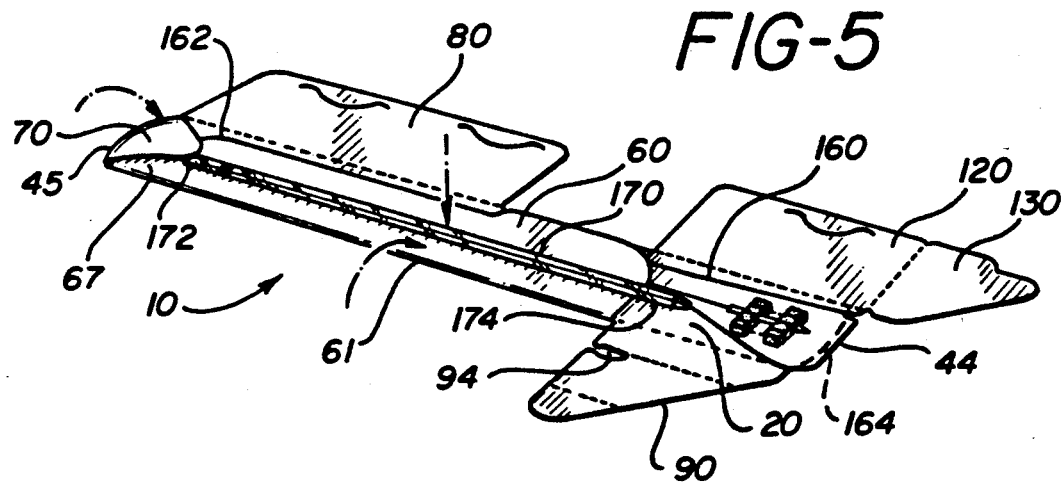

The package 10 of the present invention is assembled in the following manner. Referring to FIG. 4, the initial step in the assembly is to insert the surgical needle 150, having a suture 160 attached thereto, into the needle park 30 with the tip 151 of the needle pointing toward the top tab 44 of the central panel 20. The suture 160 is looped as shown in FIG. 4 with an initial portion of the suture coming down from the suture needle toward the bottom of central panel 20 to form loop 162 then looping upward and around the back of tab 44 to form loop 164 such that the suture 160 is engaged by tab 44 along slot 43 and side 26. Next, the first suture retaining panel 50 is folded inward toward central panel 20, thereby covering a section of the suture 160. Next, as seen in FIG. 5, inner suture retaining panel 60 is folded inward, on top of central panel 50 and lower suture loop 162. Next, the cannula 170 is placed on top of the outside of the folded inner suture retaining panel 60. The cannula 170 is positioned so that the proximal end 172 is adjacent to gusset 45 at the bottom of the central panel 20 and the distal end 174 is in longitudinal alignment with the slot 94 contained in triangularly shaped cannula retaining panel 90. It is important that the top loop 164 of the suture remains engaged by tab 44 when placing the cannula 170 into position on top of central panel 20, first suture retaining panel 50, and inner suture retaining panel 60. Then, the end tab panel 70 at the bottom of central panel 20 is folded inwardly about fold lines 47 and 49 over the proximal end 172 of the cannula 170 to form gusset 45. The end tab 70 also covers the lower curved end 67 of inner cannula retaining panel 60 when the end tab 70 is in the folded position.

Figure 6:
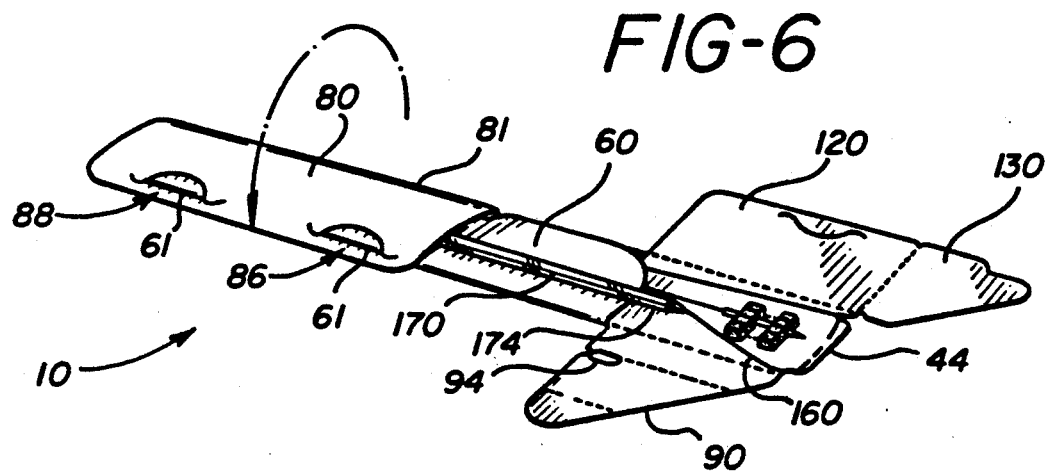

Next, as seen in FIG. 6, the outer cannula retaining panel 80 is folded inward over the end tab panel 70, the inner cannula retaining panel 60, and the cannula 170 and suture loop 162. Tabs 87 and 89 are displaced to the back, outer side of central panel 20 such that a section of the outer side of central panel 20 and a section of the outer side of inner cannula retaining panel 60 are contained along fold line 61 in the respective tab pockets 86 and 88. The next step in assembling the package, as seen in FIG. 7, is to fold triangularly shaped cannula retaining panel 90 in an inward manner such that the distal end 174 of the cannula 170 is engaged in the slot 94 by tabs 96 which are displaced downwardly behind the cannula 170.

Next, as seen in FIG. 8, upper, outer locking panel 120 is displaced in an inward direction on top of triangularly shaped cannula retaining panel 90 thereby engaging the end 112 of tab panel 110 and causing the panel 110 to fold in a backward manner upon the back side of second panel 100 about fold line 101. Then, referring to FIG. 9, tab 125 is inserted behind the back side of the central panel 120 along fold line 91 thereby causing a section of the central panel 20 and the triangularly shaped cannula retaining panel 90 to be engaged in the tab pocket 124. FIG. 9 has been rotated 180° from the orientation of the previous drawing figures to show the bottom of the package 10. Next, tab panel 130 is displaced outwardly on top of the back, outer side of central panel 20 about fold line 131, thereby covering upper suture loop 162 and tab 44. Then, end tab 135 of tab panel 130 is inserted into tab pocket 124 and the shoulder 137 is displaced behind tab 125. Finally, as seen in FIG. 10, the assembled package 10, containing the assembly 180, is placed into a conventional plastic envelope 220, preferably having one clear side, and, the envelope 220 is sealed.

Conventional plastic envelopes are made from polymer films including TYVEK ®, polyester copolymers, polypropylene copolymers, combinations thereof, and the like. The envelopes may also be made from polymer film, paper, and foil combinations. The package 10 may also be packaged in a conventional foil packet.

Figure 3:
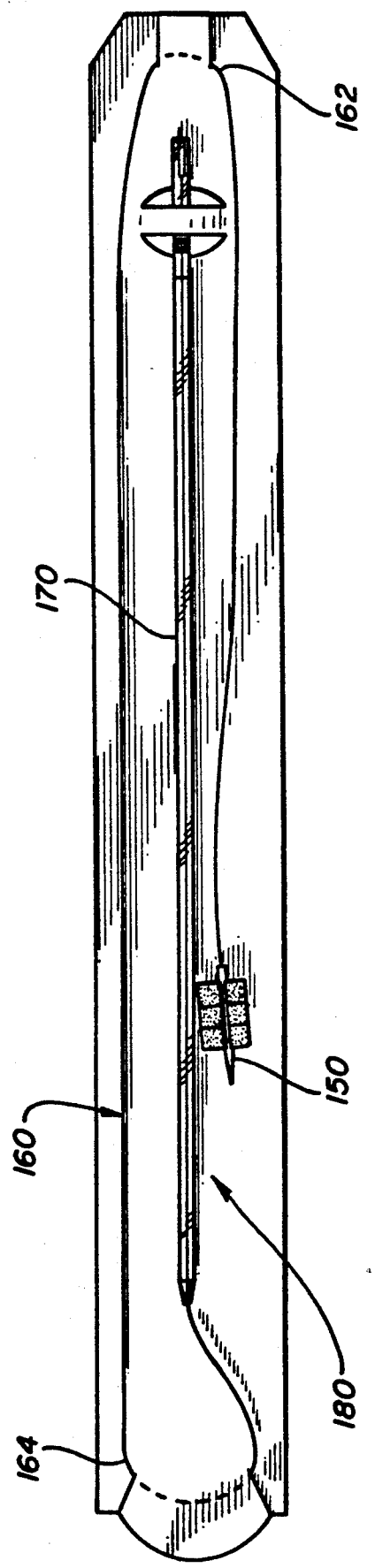
FIG. 3 is a view of a package of the prior art containing a surgical needle and suture and cannula assembly.

Referring to FIG. 3, there is illustrated a package 300 of the prior art. It can be seen that the cannula and suture and needle assembly 180 is retained in such a fashion by retaining loop 320 and slits 330 and 340 that it is not easily removed from the package without tearing the loop and maneuvering the suture out of the slits 330, 340, thereby possibly damaging the suture 160, needle 150 or cannula 170. In addition, it can be appreciated that the suture 160 in package 300 has more freedom to move around and twist then in package 10 of the present invention. This causes problems with many suture products because many conventional sutures tend to have memories, and, if the suture 160 is twisted or somehow distorted during sterilization, shipping, or handling, the suture 160 will retain the distorted shape. It is difficult for the surgeon to use such a distorted suture in an endoscopic procedure. If the suture 160 is severely distorted, the assembly 180 may be unusable and may have to be destroyed. Furthermore, the package 300 does not protect the suture during sterilization. In addition, it can be appreciated that the package 300 of the prior art will allow the cannula 170 to puncture or tear an outer plastic envelope, compromising the sterility of the contents. When the outer plastic envelope is punctured or torn, the assembly 180 is typically not capable of being sterilized at the hospital site. Therefore, once the integrity of the sterility has been compromised, it is necessary for the user to destroy the device.

The folder package 10 of the present invention overcomes the problems associated with the prior art packages. The needle 150 and suture 160 and cannula 170 are locked in place by a plurality of panels yet the suture, cannula and needle assembly 180 is easily removed from the package 20 in the sterile operating room. This is done by simply releasing the tab 125 on the upper, outer locking panel 120 and releasing the tabs 87 and 89 on the outer cannula retaining panel 80, and then lifting end tab panel 70. Triangularly shaped cannula retaining panel 90 is lifted by pulling on end 112 of tab panel 110, thereby disengaging the distal end 174 of the cannula 170 from slot 94. Then the cannula 170 is lifted so that the upper suture loop 164 is disengaged from tab 44. Next, the inner suture retaining panel 60 and the central panel 50 are opened and the entire cannula and suture and surgical needle assembly 180 can be quickly removed from the package by pulling the cannula and suture and needle assembly 180 in a rearward continuous fashion, thereby disengaging the needle 150 from the needle park 30. It will be appreciated that other opening sequences may be utilized, depending upon the preference of the user.

The folder packages 10 of the present invention are preferably constructed from any material having the required structural characteristics such that the material can be readily die cut and scored. In addition, the material must be easily folded and sterilizable. The materials include those known in the art for packaging sutures and medical devices, including paper, plastic, foils, and laminates of one or more thereof. However, it is particularly preferred in the practice of the present invention to utilize a heavyweight, relatively stiff, medical-grade paper or paperboard such as 0.007-0.016" suture board.

The package 10 of the present invention has many advantages when compared with the packages of the prior art. The package 10 of the present invention retains a cannula and suture and surgical needle assembly 180 in a secure manner in a locked package. The suture 160 is retained in a given configuration such that substantially no shifting or movement of the suture occurs. Similarly, the cannula 170 is retained in a locked position so that it does not shift during sterilization, shipping and handling and the needle 150 is similarly retained. In addition, the package 10 serves as a protective barrier for the suture during a sterilization process. The package 10 is economical to manufacture, easy to assemble, and readily adapts to typical, conventional sterilization techniques. In addition, the package 10 of the present invention for an endoscopic cannula and suture and needle assembly 180 protects a plastic overwrap 220 (as illustrated in FIG. 10 by broken lines) from being damaged during sterilization, shipping and handling by the assembly 180.

Although this invention has been shown and described with respect to the detailed embodiments thereof, it will be understood by those skilled in the art that various changes in form and detail thereof may be made without departing from the spirit and scope of the claimed invention.

What is claimed is:

1. A package comprising:
   a central panel with four sides said panel having a top and a bottom;
   a first suture-retaining panel foldably attached to a first side of the central panel;
   an outer cannula-retaining panel foldably attached to the first side of the central panel;
   an upper, outer locking panel foldably connected to the first side of central panel above the first suture retaining panel;
   a lower suture-retaining panel foldably connected to a second side of the central panel;
   an upper cannula-retaining panel foldably connected to the second side of the central panel above the lower suture-retaining panel;
   cannula locking means in the upper cannula-retaining panel for retaining a cannula;
   locking means in the outer cannula-retaining panel and the upper, outer locking panel for fastening the package; and,
   needle park means on the central panel for receiving and retaining a surgical needle.

2. The package of claim 1 wherein the needle park means comprises:
   first and second foam members, said members having slits therein for receiving and retaining a surgical needle.

3. The package of claim 1 wherein the cannula locking means in the upper cannula-retaining panel comprises a U-shaped slot having a curved end and an open end and a pair of opposed tabs at either side of the opening of the slot.

4. The package of claim 1, wherein the locking means in the outer cannula-retaining panel and the upper, outer locking panel comprise tabs and tab pockets.

5. The package of claim 4 wherein the upper, outer locking panel additionally comprises a tab panel foldably connected to the top of the upper, outer locking panel, said tab panel having an end tab section which is engaged by the tab pocket of the outer cannula-retaining panel when the package is assembled.

6. The package of claim 4 wherein the upper, outer locking panel additionally comprises a tab panel foldably connected to the top of the upper, outer locking panel, said tab panel having an end tab section which is engaged by the tab pocket of the upper, outer locking panel when the package is assembled.

7. The package of claim 1 further comprising a lower end gusset at the bottom of the central panel, formed by at least two fold lines between the central panel and an end tab panel, said end tab panel being foldably connected to the bottom of the central panel.

8. The package of claim 1 further comprising a tab extending from the top of the central panel for engaging and retaining a suture.

9. The package of claim 1 wherein the needle park means comprises,
   first and second foam members, said members having slits therein for receiving and retaining a surgical needle.

10. The package of claim 1 wherein the cannula locking means in the triangularly-shaped panel comprises a U-shaped slot having a curved end and an open end and a pair of opposed tabs at either side of the opening of the slot.

11. The package of claim 1, wherein the locking means in the outer cannula retaining panel and the upper outer locking panel comprise tabs and tab pockets.

12. The package of claim 1 further comprising a lower end gusset at the bottom of the central panel, formed by at least two fold lines between the central panel and the end tab panel.

13. A package, comprising
- a central panel having a top and a bottom, said panel having a substantially rectangular shape with two major sides and an upper minor side and a lower minor side;
- a first suture-retaining panel foldably attached, centrally, to a first major side of the central panel;
- an outer cannula-retaining panel foldably attached to the first major side of the central panel below the first suture-retaining panel;
- an upper, outer locking panel foldably connected to the central panel above the first suture-retaining panel;
- an inner suture-retaining panel foldably connected to the second major side of the central panel;
- a triangularly-shaped cannula-retaining panel foldably connected to the second major side of the central panel above the inner cannula-retaining panel;
- an end tab panel foldably connected to the lower minor side of the central panel;
- a tab extending from the upper minor side of the central panel for retaining a suture;
- cannula locking means in the triangularly-shaped panel for retaining a cannula;
- locking means in the outer cannula retaining panel and the upper, outer locking panel for fastening the package; and,
- needle park means on the central panel for receiving and retaining a surgical needle.

14. The package of claims 1 or 13, further comprising a plastic outer envelope.

15. The package of claims 1 or 13, further comprising a foil packet.

* * * * *